United States Patent [19]

Harris

[11] Patent Number: 4,463,090

[45] Date of Patent: Jul. 31, 1984

[54] CASCADE AMPLIFICATION ENZYME IMMUNOASSAY

[76] Inventor: Curtis C. Harris, 8402 Thornden Ter., Bethesda, Md. 20034

[21] Appl. No.: 307,324

[22] Filed: Sep. 30, 1981

[51] Int. Cl.$^3$ .................. G01N 33/54; C12Q 1/56; C12Q 1/38; C12N 9/96
[52] U.S. Cl. ............................ 435/7; 435/13; 435/23; 435/188; 435/810; 435/24; 436/829
[58] Field of Search ............... 424/1, 8, 12; 435/7, 435/188, 810, 23, 24, 13; 23/230 B; 436/536, 537, 829

[56] References Cited

U.S. PATENT DOCUMENTS

| | | | |
|---|---|---|---|
| 3,654,090 | 4/1972 | Schunrz et al. | 435/7 |
| 3,966,556 | 6/1976 | Rubenstein et al. | 435/7 |
| 4,056,519 | 11/1977 | Bobbitt et al. | 435/23 |
| 4,193,983 | 3/1980 | Ullman et al. | 435/7 |
| 4,233,402 | 11/1980 | Maggio et al. | 435/7 |
| 4,275,149 | 6/1981 | Litman et al. | 23/230 B |
| 4,289,748 | 9/1981 | Harris et al. | 435/7 |
| 4,327,710 | 7/1982 | DeLoach et al. | |
| 4,334,018 | 6/1982 | Kirchhof | 435/23 |
| 4,366,241 | 12/1982 | Tom et al. | 435/7 |
| 4,376,165 | 3/1983 | Hornby et al. | 435/7 |

OTHER PUBLICATIONS

Barlow, "Urinary and Kidney Cell Plasminogen Activator", *Methods in Enzymology*, vol. XLV (1976) pp. 239-243.
Castellino et al., "Streptokinase", *Methods in Enzymology*, vol. XLV (1976) pp. 244-257.
Robbins et al., "Plasminogen and Plasmin", *Methods in Enzymology*, vol. XLV (1976) pp. 257-273.
Richter et al., "Simulation of Coupled Enzyme Assays for Clotting Factors and its Application to a New Method for Determination of Human Plasminogen", *Computers and Biomedical Research*, vol. 11, (1978) pp. 133-146.
Selkurt, et al., *Basic Physiology for the Health Sciences*, Little, Brown and Company Boston (1975) pp. 340-345.
Biggs, et al., *Human Blood Coagulation, Haemostusis and Thrombosis*, 2nd ed., Blackwell Scientific Publications, London, (1976) pp. 49-54.
Walsh, *Enzymatic Reaction Mechanisms*, W. H. Freeman and Company, San Francisco (1979) pp. 116-170.
Zimmerman, et al., "Direct Flourescent Assay of Urokinase and Plasminogen Actuators of Normal and Malignant Cells: Kinetics and Inhibitor Profiles", *Proc. Nat. Acad. Sci. USA.*, vol. 75, No. 2, (1978), pp. 750-753.
Pochron, et al., "A Flourescent Substrate for Plasminogen", *Thombosis Res*, vol. 13, No. 5, (1978), pp. 733-739.
Haga, et al., "Analytical Biochemistry" 118: 286-293 (1981).

*Primary Examiner*—Esther M. Kepplinger
*Attorney, Agent, or Firm*—Holman & Stern

[57] ABSTRACT

The invention provides enzyme immunoassays whose sensitivity is increased by cascade amplification. The coupled ligand (enzyme or an activator) catalytically activates a second enzyme which acts on a substrate or can act on a third enzyme to produce a cascade. Alternatively, a proenzyme is coupled to the ligand and converted by an activator to an enzyme which is itself an activator of a second proenzyme in a cascade.

17 Claims, No Drawings

CASCADE AMPLIFICATION ENZYME IMMUNOASSAY

BACKGROUND OF THE INVENTION

1. Field of the Invention

This invention relates to enzyme immunoassays whose sensitivities are greatly increased by cascade amplification.

2. Description of the Prior Art

Single-stage enzyme amplified immunoassays are well known and are disclosed in books such as "immunoassays in the Clinical Laboratory", Nakamura, et al., (ed.) Alan R. Liss, Inc., N.Y.C. (pub.) (1979); "immunoassays-Clinical Laboratory Techniques for the 1980's", Nakamura, et al., (ed.), Alan R. Liss, Inc., N.Y.C. (pub.), (1980); and "The Tools of Biochemistry", Cooper, John Wiley & Sons, N.Y.C. (pub.), (1977); among others.

U.S. Pat. No. 3,654,090 (Schuurs, et al.,) discloses enzyme assays for the determination of antigens and antibodies, comprising using a reagent consisting of one component of an antigen-antibody reaction in an insolubilzed form and the other one cavalently linked to an enzyme. There is further disclosure of quantitative assays using colorimetry, spectrophotometry, fluorospectrophotometry or gaseometry, and qualitative assays using either a colored substrate or a colored end product. At column 2, lines 32-42 it is stated that: "Further possibilities are: The conjugated enzyme generates the substrate for a second enzyme, which gives a coloured end-product. The conjugated enzyme converts a pro-enzyme into an enzyme, which catalyses a reaction with a coloured compound involved. The conjugated enzyme catalyses a reaction wherein substrate or end-product can be stained easily. Many enzymes can be used in reactions as described above, such as peroxidase, $\beta$-glucuronidase, $\beta$-D-glucosidase, $\beta$-D-galactosidase, urease, glucose oxides + peroxidase, and galactose oxidase + peroxidase".

U.S. Pat. No. 3,966,556 (Rubenstein, et al.,) [and related U.S. Pat. Nos. 3,817,837; 3,875,011; 4,190,496; 4,191,613; and 4,203,802] disclose enzyme assays in which an enzyme is bound to a ligand or ligand counterfeit. A receptor when bound to the enzyme-bound-ligand substantially inhibits enzymatic activity, providing for different catalytic efficiencies of enzyme-bound-ligand with and without the receptor. There is no disclosure of cascade amplification.

Other U.S. patents that disclose enzyme assays (but without cascade amplification) include: U.S. Pat. Nos. 3,791,932; 3,839,153; 3,850,752; 4,002,532; 4,043,872; 4,134,792; 4,228,237; and 4,238,565.

Also well known, is the general concept of the "cascade phenomenon", whereby there is a sequential activation of enzymatic components. The best known example of an enzymatic cascade is the process of blood clotting [see, for example, "Basic Physiology for the Health Sciences", Selkart (ed.), Little, Brown and Company, Boston (pub.) (1975) at pages 340-345; and "Human Blood coagulation, Haemostasis and Thrombosis", Biggs (ed.), 2nd ed., Blackwell Scientific Publications, London (pub.) (1976)]. In "Human Blood Coagulation, etc.", supra, there is disclosed at pages 49-54 an assay for measuring prothrombin comprising activation of the proenzyme prothrombin to the enzyme thrombin by thrombokinase, and the subsequent conversion of fibrinogen to fibrin by the thrombin. Since enzymes are true catalysts and each enzyme molecule acts on a number of molecules causing a multiplier effect, a two stage cascade causes a geometric increase in the molecules that are acted upon. In "Enzymatic Reaction Mechanisms", Walsh, W. H. Freeman and Company, San Francisco (pub.) (1979) at pages 116-170, there is the statement: "This process is called a *cascade phenomenon* (sequential activation of components), and this is only one example of many such phenomena in enzymatic systems (the process of blood clotting and the mobilization of glycogen being two others) where such complex sequences operate. It has been argued that cascade systems are sensitive ways of amplifying an initial small biological signal. Because each component in the cascade is a catalytic entity, one can have large multiplication factors at each step".

"Methods in Enzymology" XLV, Lorand (ed.), Academic Press (pub.) (1976) at pages 239-273 discloses the activation of plasminogen to plasmin by urokinase (pp. 242-243) and by streptokinase (pp. 245-246); and the use of caseinolytic and fibrinolytic substrates (pp. 257-258). In Thrombosis Research, 13:733-729 (1978) there is disclosed a fluorescent substrate assay for plasminogen after its conversion to plasmin by streptokinase. The specific fluorescent substrate disclosed is H-D-valine-leucine-lysine-5-amidoisophtholic acid dimethyl ester di-tri-fluoroacetate, and comparison was made with a caseinolytic assay and a radial immunodiffusion assay. In Proc. Natl. Acad. Sci. USA 75:750-753 (1978) a similar assay is disclosed using a synthetic fluorogenic peptide substrate, 7-(N-Cbz-Glycylglycylarginin-amido)-i-methylcoumarin trifluoroacetate. In Thrombosis Research 13:389-395 (1978) there is disclosed a solid phase assay for fibrinogen activators (i.e., streptokinase and urokinase) using $^{125}$I labeled fibrinogen. There is no disclosure of the coupling of ligands to the fibrinogen. In Comp. and Biomed. Res. 11:119-132 (1978) there is a discussion of blood clotting enzyme cascades in connection with a plasminogen-plasmin assay using streptokinase as the activator.

SUMMARY OF THE INVENTION

This invention provides enzyme immunoassays whose sensitivity is greatly increased by cascade amplification.

In one embodiment, a conventional enzyme immunoassay of any type is amplified by causing the coupled ligand (i.e., an enzyme or other activator) to activate catalytically a second enzyme, which second enzyme acts upon a substrate, thus affording a two stage enzyme cascade.

In another embodiment, the second enzyme activates a third enzyme, which third enzyme acts upon a substrate, thus affording a three stage enzyme cascade.

In a third embodiment, a first proenzyme is the coupled ligand and is converted by an activator to an enzyme. This enzyme is one which is itself an activator of a second proenzyme in a cascade. Since most enzyme activators of proenzymes are themselves proteases that might self-degrade during storage of the coupled ligand, the use of a proenzyme coupled ligand is preferred to prevent such autolysis.

In all instances, the activation must be catalytic in nature, so that the activator is free to operate upon a large number of molecules, thus achieving a multiplier effect for each stage of the enzymatic reaction. The result is a geometric increase in the number of activated molecules and a corresponding geometric increase in the sensitivity of the assay.

The initial enzyme catalysis may be activated by proenzyme-enzyme activation, coenzyme-enzyme activation, or suitable change in the proenzyme environment, such as pH adjustment. The second enzyme catalysis, to form the cascade amplification contemplated by this invention, must be activated by the first enzyme, the third enzyme by the second enzyme.

As in conventional in immunoassays, the quantitation may be in terms of the amount of a suitable substrate acted upon, in this instance, by the final enzyme in the cascade.

For the purposes of this invention, the term "proenzyme" will be used to designate any inactive or less active form of an enzyme which may be acted upon in any manner to be activated or made more active. In this context, "active" refers to catalytic activity. Where the proenzyme must be activated by another substance, that substance will be referred to as an "activator". Thus, the basic mechanism of the assays of this invention may be depicted as:

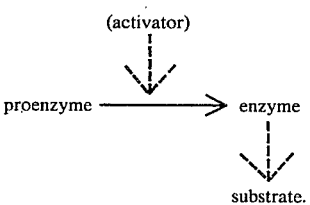

Further, for the purpose of this invention, the term "proenzyme" includes any active enzyme which is rendered inactive by encapsulation in liposomes and for which the activator is one which catalytically cleaves said liposomes.

Additionally, for the purposes of this invention, the term "proenzyme" includes any enzyme which is activated or made more active by a coenzyme or cofactor, in which instance the activated enzyme shall be referred to as an enzyme. Consequently, any enzyme which is inactive or will be made more active, shall be referred to as a proenzyme.

The terms "proenzyme", "enzyme", "activator", and "substrate" have been defined as above to facilitate the description of this invention, it being understood that they may have slightly different meanings outside the scope of this invention and that it is not intended to limit this invention by the use of any other definitions of these terms.

For the purposes of this invention the catalytic activity of the enzyme upon a substrate is defined as the "first stage" and the conversion of the proenzyme to an enzyme by the catalytic action of the activator is defined as the "second stage". As used herein, the term "cascade" refers to the combination of at least two sequential catalyses, the last of which (i.e., the first stage) is upon a substrate.

It is also possible, according to this invention, for three or more catalyses to be used in sequence. For example, the activator may itself be an enzyme which has been catalytically activated from a proenzyme. The mechanism of such an assay may be depicted as:

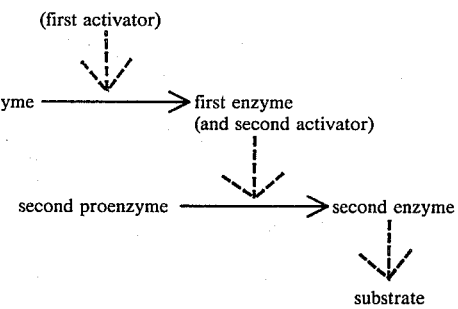

The above assay would be typical of a "three-stage" assay according to this invention, in which the "third stage" (which is the first chronological step) is the catalytic activation of a "first proenzyme" to a "first enzyme" by a "first activator". The "second stage" is the catalytic activation of a "second proenzyme" to a "second enzyme" by a "second activator", which second activator must be the first enzyme. The "first stage" is the catalytic action of the second enzyme upon the substrate.

It must be apparent that four or more stages can be afforded by using additional proenzyme - enzyme catalytic activations, always with the proviso that the enzyme produced in one stage is the activator for the proenzyme of the next stage, until the final stage in which the catalytic action is upon the substrate.

To afford the immunoassays of this invention, either the first proenzyme or the first activator in the sequence must be coupled to a antibody or antigen, in any conventional manner.

The result of the assay is determined from the change (if any) in the substrate. Where the assay is qualitative, or approximately quantitative, a colorimetric substrate is preferred. This would afford an assay which is both simple and inexpensive because a visual determination would be adequate, and which therefor could be packaged in kit form for clinical or individual use. Another particularly useful substrate would be one which is fluorescent. Other substrates which may be utilized, where greater quantitative determination is desired in a clinical or research laboratory include radioactive, chemiluminescent and electron spin resonance substances. It would even be possible to use a substrate which coagulated when acted upon, and to measure the result by the presence, absence, or size, of a clot.

The enzymes which are useful in this invention are all enzymes which have an inactive or less active proenzyme form, and which may be activated either by an activating substance or by manipulation of the environment. It is also possible to utilize any enzyme which does not have a less active form by encapsulating it in liposomes and cleaving the liposomes in a catalytic manner. A liposome-encapsulated enzyme may be substituted for any stage of the assays of this invention.

The 1978 Recommendations of the Nomenclature Committee of the International Union of Biochemistry as to the classification of enzymes are utilized in the description of this invention. All enzymes are classified into six main divisions, which are: Oxidoreductases, Transferases, Hydrolases, Lyases, Isomerases and Ligases (Synthetases). Enzymes falling into all of these divisions are useful in this invention, provided that either they also occur in a less active or inactive form or that they can be encapsulated in liposomes. The preferred divisions are Transferases and Hydrolases, with Hydrolases being most preferred. Within Hydrolases (Division 3.0), the preferred subclass is 3.4 (Peptide Hydrolases, i.e., acting on peptide bonds) and within this subclass the most preferred sub-subclasses are 3.4.21 (Serine Proteinases, i.e., having an active center histidine and serine involved in the catalytic process) and 3.4.23 (Carboxyl Proteinases, i.e., having a pH optimum below 5 due to the involvement of an acidic residue in the catalytic process). For encapsulation in liposomes, the preferred division is Oxidoreductases. Activation of the above enzymes is preferably by a suitable kinase.

In another embodiment of this invention, it is possible to have a cascade in which the enzyme produced in the first stage is itself a proenzyme, rather than an activator for a proenzyme. For example, where the second proenzyme is angiotensinogen, which is catalytically activated by renin (3.4.99.19) to the second enzyme angiotensin I, this second enzyme may also function as a first proenzyme in that it may be catalytically further activated by dipeptidyl carboxypeptidase (3.4.15.1) to the most active angiotensin II, which may then act catalytically on a suitable substrate, such as hip-his-leu acylated tripeptide or hip-gly-gly acylated tripeptide, in the following manner.

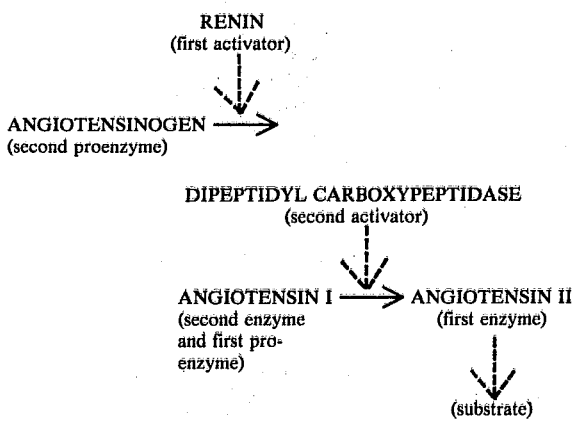

In the above assay, either of the complements, the angiotensinogen or the renin, may be the coupled ligand, and the remaining complement together with the depeptidyl carboxypeptidase and the substrate may be added in sequence or, all may be present initially in an assay broth.

It is also possible to use any one or more of the enzymes involved in blood coagulation cascades, intrinsic or extrinsic and using any known pathway, and all of these are within the general scope of this invention.

DESCRIPTION OF THE PREFERRED EMBODIMENTS

The assays of this invention may be used for the qualitative and/or quantitative measurement of any substance which may be assayed using an antibody-antigen reaction (i.e., an immunoassay). The primary difference between the assays of this invention and conventional enzyme-linked immunoassays is that in a conventional enzyme-linked immunoassay, the coupled enzyme acts directly upon a substrate, and the reaction is measured by the change in that substrate. In striking contrast, the cascade assays of this invention are amplified by at least on enzyme catalysis, before the substrate is acted upon by an enzyme.

The average turnover number for enzymes commonly used in enzyme immunoassays is 1,000 min$^{-1}$ (i.e., 1,000 moles of substrate reacted per minute per mole of enzyme active site). Where the substrate normally used in an enzyme immunoassay is substituted by a molecule that is itself converted to an enzyme, the turnover rates are multiplied by each other [i.e., (1,000 min$^{-1}$)×(1,000 min$^{-1}$) or 1,000,000 min$^{-1}$], and when the substrate-enzyme activates a second substrate to an enzyme, the geometric multiplication of the turnover rate is, e.g., (1,000 min$^{-1}$)×(1,000 min$^{-1}$)×(1,000 min$^{-1}$) or 1,000,000,000 min$^{-1}$. These multiple rate accelerations enormously increase the sensitivities of the assays according to this invention.

Any type of conventional immunoassay technique may be used in this invention, including, but not limited to, a direct assay, an antibody bridge assay, a solid phase assay, a sandwich assay, a competitive assay, etc.

The "*activator*" ligand of this invention is coupled in the same manner and position as the enzyme in a conventional enzyme immunoassay. However, the ligand acts to activate an enzyme, which then may activate at least one second enzyme, which acts upon a substrate. Where the activator ligand is itself an enzyme, it may activate a second enzyme, which acts directly upon the substrate. The various types of activator ligands according to this invention are as follows.

The ligand may be an activator for a proenzyme to an enzyme, in which instance the proenzyme must be present during the assay.

The ligand may be a proenzyme itself, in which instance the proenzyme activator must be present during the assay.

The ligand may be an enzyme itself which acts as an activator for a second enzyme, in which instance the second enzyme must be present during the assay.

The ligand may be a coenzyme, in which instance the enzyme it activates must be present during the assay.

The ligand may be an inactive enzyme activated by a coenzyme, in which instance the coenzyme must be present during the assay.

The ligand may be an inactive enzyme activated by another activating enzyme, in which instance the activating enzyme must be present during the assay.

The ligand may be a moiety which alters the pH of the assay broth to activate an enzyme, in which instance the broth must have a starting pH of about 7 and the enzyme to be activated must be present.

Other ligands may be moieties which activate an enzyme by altering the ionic strength, salt concentration, electromagnetic forces, etc., of the assay broth; or which are sensitive to changes in the physical environment such as increased actinic or other radiation and which are activated upon such changes to act upon an enzyme, etc.

In all instances, the activator ligand will have no effect unless the receiver molecule with which it reacts is present. Thus, the receiver molecule may be added to the assay broth after the coupled ligand is believed to be present, or may be present ab initio, since the assay reaction cannot proceed if the activator ligand is absent, thus indicating the absence of the substance being assayed.

The cascades of this invention are preferably the result of the product of the activator-receiver reaction catalyzing a subsequent enzyme by activating it, which subsequent enzyme acts upon a substrate. The amount of change in the substrate is then quantified in a conventional manner. As discussed above, it is also possible that the activator-receiver reaction product is itself a partially activated enzyme (i.e., another proenzyme), which is then further activated catalytically.

It is particularly emphasized that this invention is not limited by the type of assay (i.e., sandwich, competitive, etc.) and may be used with equal efficacy regardless of the type of assay or the type of substrate. Thus, the invention lies in the amplification of the assay by any of the described embodiments.

An example of a sandwich assay according to this invention is as follows:

1. Either one of an antibody-multivalent antigen pair is attached to a solid phase.
   (a) if the antibody is attached, the tested multivalent antigen is coupled to the attached antibody, and a ligand-coupled antibody is then coupled to another active antigen site on the multivalent antigen.
   (b) if the tested multivalent antigen is attached to the solid phase, the ligand-coupled antibody is attached to another active antigen site on the multivalent antigen.

The ligand is in this instance, an activator for a proenzyme.

2. The first proenzyme to be activated is already present or is added, and if the tested multivalent antigen is present, the ligand-coupled antibody will also be present, and the ligand will activate the first proenzyme to a first enzyme, thus affording a first multiplier stage.

3. Optionally, the activated first enzyme will be chosen so that its substrate is a second proenzyme, already present or to be added, which will be activated by the first enzyme to a second enzyme. Since the activation is a catalytic action, the first enzyme acts upon a number of second proenzyme molecules, activating them to second enzyme molecules, thus affording a second multiplier stage.

4. At this point, a suitable substrate may be provided (already present or to be added) to be acted upon by the second enzyme. The change in the substrate is then measured in a conventional manner, and is an additional multiplier stage.

5. Alternatively, a third proenzyme may be provided (already present or to be added) instead of the above substrate, which third proenzyme must be chosen so that it is activated by the second enzyme. The activation by the second enzyme being catalytic in nature, the second enzyme acts upon a number of third proenzyme molecules to yield a number of third enzyme molecules, thus affording a third multiplier stage.

6. At this point, a suitable substrate may be provided (already present or to be added) to be acted upon by the third enzyme. The change in the substrate is then measured in a conventional manner, and is an additional multiplier stage.

In all of the above steps, the activations are sequential and will not proceed if any step is omitted. Thus, if the antigen or antibody to be detected or quantitated is absent, none of the sequential steps will take place. For this reason, it may be convenient for all of the sequential reagents to be present simultaneously. Thus, for example, the first proenzyme, second proenzyme, and substrate, may all be present. Since the solid phase is washed thoroughly after the ligand-coupled antibody or antigen is added, the absence of the antigen or antibody to be detected will result in the complete absence of the activator ligand, and therefore none of the cascade steps will occur.

Quantification of the antibody or antigen to be tested is easily done by comparing the substrate measurement with that of a standard derived from the cascade amplification assay measurement of given incremental amounts of the same antibody or antigen to be tested.

The measurement of the change in substrate may be by any conventional means. One means is the use of a substrate that changes color after it is acted upon by the final enzyme in the cascade. The amount of color change, measured against a standard, will quantitate the amount of the assayed substance. A colorimetric determination has the advantage of not requiring any laboratory measuring equipment, since color gradations can be compared to the standard with the unaided eye. It would also be possible to use a spectrophotometer to make objective colorimetric determinations with even greater sensitivity.

Another means of measurement is by using a labeled substrate. The substrate marker can be a radioactive label ($^{14}C$, $^{3}H$, $^{35}S$, $^{125}I$, $^{131}I$, etc.), in which instance the measurement is by a radiation counter or perhaps by autoradiography. The substrate marker can be a fluorescent label (based on a fluorogenic dye-analyte conjugate, etc.) with a measurement of fluorescent intensity. The substrate marker can be an electron spin label (i.e., a nitroxide spin label such as a piperidinyl, pyrollidinyl, oxazolidinyl, maleimide, iodoacetamide, or isothiocyanate moiety, etc.), with a measurement of intensity by an electron spin resonance spectrometer.

Obviously, where the label is only activated when the tested substrate is present (such as in colorimetry), no further rinsing of the assay is required. Where, however, the substrate is a radioactive label or electron spin label, a separate step must be performed to remove all non-acted-upon substrate. Additionally in such an instance, the acted-upon substrate must bind to the solid phase or to some other portion of the assay container, so it is not eluted with the non-acted-upon substrate.

In still another embodiment of this invention, the first enzyme coupled to the antibody or antigen is a carboxylic ester hydrolase, preferably lipase (3.1.1.3) or phospholipase ($A_1,A_2,B,C,D$) (3.1.1.32,4,5,3). Liposomes are added or initially present in the assay broth. Liposomes are lipid-filled sacs which are either natural or synthetic, and which may contain large numbers of the molecules of a second enzyme, preferably in excess of $10^3$. The preferred second enzyme is alkaline phosphatase or peroxidase. The coupled first enzyme will be present if the assay is positive, and will catalytically cleave the liposomes, thus releasing the second enzyme. A substrate is added, or intially present, which can be acted upon by the second enzyme, but not the first enzyme, and the change in the substrate is measured. If the first enzyme cleaves the liposomes at a rate of, for example, $10^2$, and each liposome contains about $10^3$ molecules of the second enzyme, the geometric cascade amplification acting upon the substrate will be $(10^3)\times(10^2)$, or $10^5$. The combined use of a liposome containing an enzyme, proenzyme, coenzyme or activator with a substance that catalytically cleaves the liposome, may be substituted for any stage of the cascade assays of this invention. In one embodiment, the catalytic cleaving substance may be coupled to the antigen or antibody of the assay. In another embodiment, the catalytic cleaving substance may be the end product of proenzyme-enzyme or coenzyme + enzyme reactions or may be a segment of a substrate acted upon by an enzyme produced in a prior stage.

As a specific example, lipase is coupled to an antibody and the assay is for the corresponding antigen. If the assay is positive the antibody-antigen coupling will result in the presence of the lipase ligand. When liposomes are also present (added to the assay broth) they are catalytically cleaved by the lipase resulting in a first stage multiplication. The liposomes may contain a substance that is a colorimetric indicator, a resonance spin indicator, etc., the measurement of which provides the assay of the antigen. In another embodiment example, the liposomes may contain molecules of a proenzyme that is only activated by a proenzyme activator (also present) when the liposome is cleaved. This will provide a two-stage (cascade) multiplication effect. The activated proenzyme can be measured by its action on a suitable substrate. Instead of a proenzyme, the liposome may contain the proenzyme activator, in which instance the proenzyme must be present in the assay broth. Similarly, the liposome may contain a coenzyme or the enzyme upon which it acts (the remaining item of the pair always being present in the assay broth), a suitable substrate for an enzyme present in the assay broth, etc.

The liposomes useful in this invention may be synthetically formed in any manner, such as by mixing enzymes with lipids at high temperature with the subsequent formation of liposomes incorporating the enzyme upon cooling. Naturally occurring liposomes may also be used, for example, human or animal erythrocytes. Erythrocytes contain a large amount of natural enzymes, especially carbonic anhydrase and lactic dehydrase. By using erythrocytes in combination with a suitable cleaving agent generated in a prior stage and with a suitable substrate for the erythrocyte enzymes, a simple and relatively inexpensive immunoassay is afforded.

Flow Outlines of Typical Assays According to this Invention

In the following assays, only the activation and catalysis is shown. In each instance, either the first proenzyme or coenzyme or the first activator may be the coupled ligand.

1. A two-stage cascade assay:

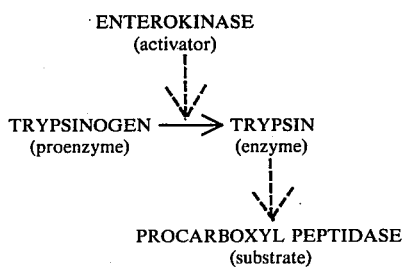

2. A two-stage cascade assay:

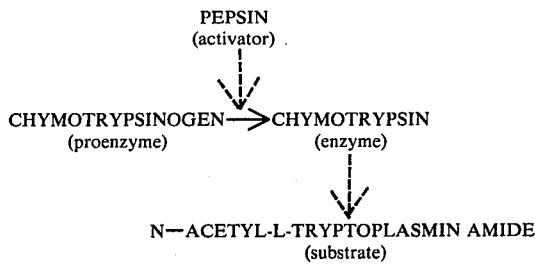

—continued

3. A three-stage cascade assay:

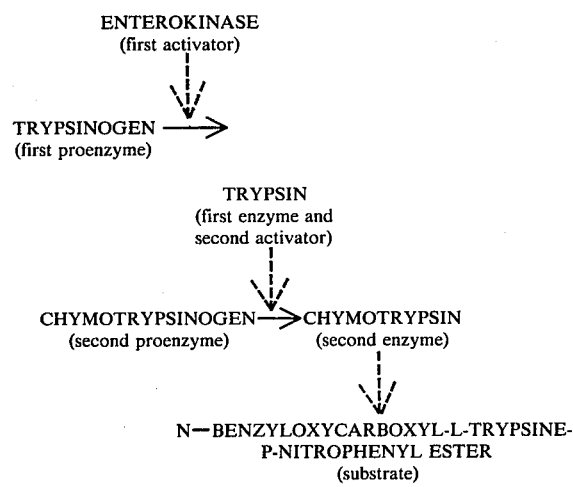

4. A three-stage cascade assay:

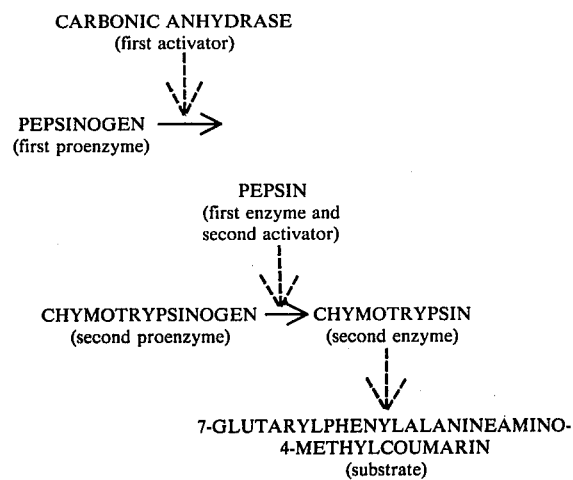

5. A two-stage cascade radioassay:

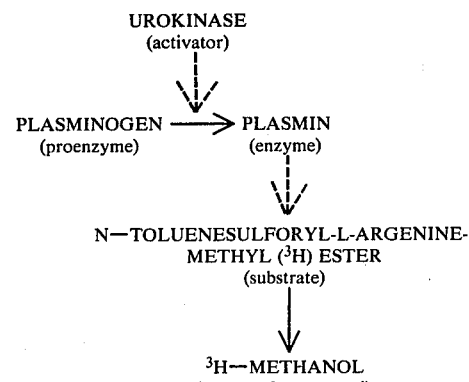

6. A three-stage cascade assay:

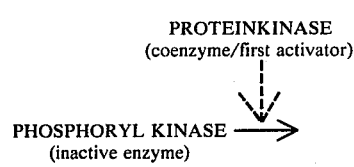

-continued

PHOSPHORYL KINASE
(activated enzyme and
second activator)

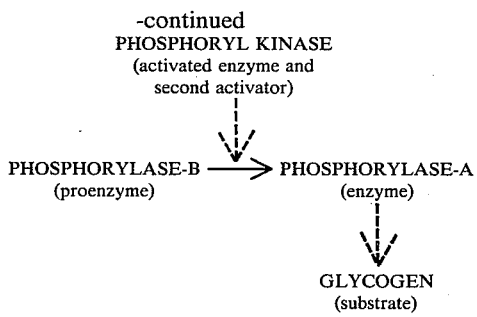

7. A three-stage cascade assay:

THROMBOKINASE
(first activator)

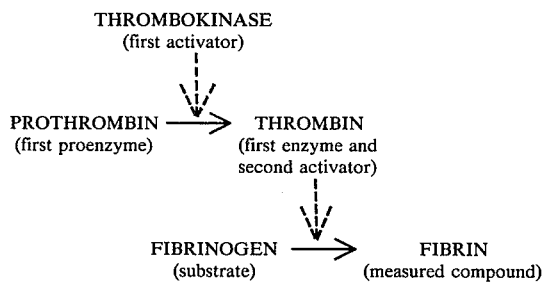

8. A three-stage cascade radioassay:

STREPTOKINASE
(first activator)

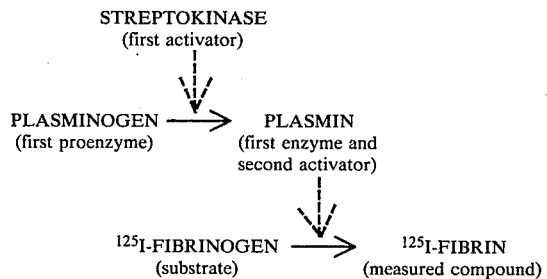

SUMMARY STATEMENT OF THE INVENTION

In a first embodiment, this invention provides in a conventional enzyme immunoassay having a coupled fully active enzyme ligand, the improvement comprising a multistage cascade assay with two stages:

using either one of the complement pair of
(i) a first proenzyme, or
(ii) a first activator for the first proenzyme, as the coupled ligand instead of a conventional fully active enzyme;

inducing a second-stage catalysis by providing the remaining of the complementary first proenzyme or first activator so as to afford a catalytic activation of the first proenzyme to a first enzyme when the assayed substance is present;

inducing a first-stage catalysis when the assayed substance is present by providing a substrate responsive to the first enzyme; and measuring the change in said substrate when the assayed substrate is present;

whereby the sensitivity of the assay is geometrically increased by the multiplication of the second-stage turnover rate and the first-stage turnover rate.

In a second embodiment, this invention provides an improvement wherein a three-stage cascade assay of the preceding type is afforded by:

using either one of the complement pair of
(i) a second proenzyme, or
(ii) a second activator for the second proenzyme, as the coupled ligand instead of a fully active enzyme;

inducing a third-stage catalysis by providing the remaining complementary second enzyme or second activator so as to afford a catalytic activation of the second proenzyme to a second enzyme when the assayed substance is present; and inducing the second-stage catalysis by providing a first proenzyme capable of being catalytically activated to a first enzyme by the second enzyme;

whereby the sensitivity of the assay is geometrically increased by the multiplication of the third-stage turnover rate, the second-stage turnover rate, and the first-stage turnover rate.

In a third embodiment, this invention provides an improvement wherein a four-stage cascade assay of the preceding type is afforded by:

using either one of the complement pair of
(i) a third proenzyme, or
(ii) a third activator for the third proenzyme, as the coupled ligand instead of a fully active enzyme, inducing a fourth-stage catalysis by providing the remaining complementary third enzyme or third activator so as to afford a catalytic activation of the third proenzyme to a third enzyme when the assayed substance is present; and inducing the third-stage catalysis by proving a second proenzyme capable of being catalytically activated to the second enzyme by the third enzyme;

whereby the sensitivity of the assay is geometrically increased by the multiplication of the fourth-stage turnover rate, the third-stage turnover rate, the second-stage turnover rate, and the first-stage tunover rate.

In any one of the three preceding embodiments, it is a preferred embodiment of this invention that each proenzyme is selected from one of the group consisting of inactive or less active forms of enzymes which are oxidoreductases, transferases, hydrolases, lyases, isomerases or ligases, or active forms of said enzymes encapsulated in liposomes.

In the preceding embodiment, it is a further preferred embodiment of this invention that each proenzyme is selected from one of the group consisting of inactive or less active forms of enzymes which are transferases or hydrolases, or oxidoreductases encapsulated in liposomes.

In the preceding embodiment, it is a particularly preferred embodiment of this invention that the proenzymes are inactive or less active forms of enzymes which are hydrolases, especially peptide hydrolases, of which the serine proteases or carboxyl proteases are the most preferred.

This invention also includes assay diagnostic kits which are combinations of any of the disclosed non-coupled proenzymes, enzymes, and activators in further combination with a coupled ligand and a substrate (where appropriate); all of the ingredients being afforded in a single mixture which remains inactive until the assayed substance is introduced.

In other embodiments of this invention, the coupled ligand is preferably either a proenzyme or an activator.

The following table gives various proenzyme - activator - enzyme - substrate combinations which are within the scope of this invention, although it should not be considered as limiting. Preferred species are indicated by the symbol #.

TABLE I

| proenzyme | activators | enzyme | substrates/notes |
|---|---|---|---|
| pepsinogen | carbonic anhydrase (4.2.1.1) acidification of the assay broth (only the proenzyme is coupled) | pepsin A,B,C (3.4.23.1,2,3) | chymotrypsinogen (#) haemoglobin (for pepsin C) N—acetyl-L-phenylalanyl-3,5-diiod-L-tyrosine bis-p-nitrophenyl sulfite [(p-NO$_2$—$\phi$—O)$_2$SO] |
| prothrombin | thrombokinase (3.4.21.6) prothrombin-activating proteinase (3.4.99.28) | thrombin (3.4.21.5) | fibrinogen (#) α-N—benzoyl-L-arginine ethyl ester hydrochloride p-toluenesulfonyl-L-argenine methyl ester benzyloxycarbonyl-glycyl-L-prolyl-L-arginyl-anilide |
| fibrinogen (properly a substrate and not a proenzyme) | thrombin (fibrinogenase) (3.4.21.5) Agkistrodon serine proteinase (3.4.21.28) plasmin (3.4.21.7) | fibrin (product) | fibrin is not an enzyme and therefore is measured directly rather than by its action on a substrate |
| trypsinogen | enterokinase (#) (3.4.21.9) trypsinogen kinase (3.4.23.6) peptidase A (3.4.23.6) | trypsin (3.4.21.4) | chymotrypsinogen (#) procarboxyl peptidase (#) p-tosyl-L-argenine methyl ester L-lysyl-p-nitroanilide α-N—benzoyl-L-arginine ethyl ester hydrochloride N—acetylglycine ethyl ester |
| chymotrypsinogen A,B | trypsin (3.4.21.4) pepsin A,B,C (3.4.23.1,2,3) | chymotrypsin A,B (3.4.21.1) | N—acetyl-L-tryptoplasmin amide N—benzyloxycarboxyl-L-tyrosine-p-nitrophenyl ester 7-glutarylphenylalanine-amido-4-methylcoumarin aminoacyl esters and amides, generally |
| chymotrypsinogen C | | chymotrypsin C | N—tosyl-L-leucine chlormethylketone (3.4.21.2) |
| plasminogen | streptokinase (#) urokinase (#) (3.4.21.31) staphylokinase (3.4.24.4) cytofibrokinase plasmakinase (Factor XII) | plasmin (3.4.21.7) | O—valine-leucine-lysine-5-amidoisophthalic acid fibrinogen (#) benzyloxycarbonyl-glcyl-L-proly-L-arginyl-anilide TAME (N—α-toluenesulforyl-L-argenine methyl ester) (#) 7-(N—Cbz-glycl-glycl-arginin-aminodo)-4-methyl-coumarintrifluoroacetate |
| prochymosin (Prorennin) | acidification of the assay broth (only the proenzyme is coupled) | chymosin (rennin) (3.4.23.4) | casein |
| inactive serine hydroxymethylase | tetrahydrofolate cofactor | active serine hydroxymethylase | L-serine (converts to glycine) |
| prokallikrein | Factor XIIa (active Hageman Factor) | kallikrein | serine proteases generally α-N—benzoyl-L-argenine ethyl ester (#) benzoyl-L-prolyl-L-phenylalanyl-L-arginyl-anilide |
| kininogen | kallikrein (3.4.21.8) kaolin | kinin | kinin is not an enzyme and therefore is measured directly rather than by its action on a substrate |
| Factor XII (inactive Hageman Factor) | kallikrein (3.4.21.8) | Factor XIIa (active Hageman Factor) | prokallikrein |
| angiotensinogen (inactive) | renin (3.4.21.8) | angiotensin I (partially activated) | only utilized in the early stage of a 3 or more stage cascade, as the proenzyme in the next stage |
| angiotensin I (partially activated) | dipeptidyl carboxypeptidase | angiotensin II (fully activated) | actylated tripeptides, particularly hip—his—leu and hip—gly—gly |

I claim:

1. In an enzyme immunoassay wherein a fully active enzyme ligand is coupled to an immuno-reactive substance which will react with an assayed substance when said assayed substance is present, and a substrate for the fully active enzyme is provided, which substrate can be catalyzed by said enzyme only if such reaction has occurred, the improvement wherein a three-stage cascade assay is performed by:
   using either one of the complement pair of
   (i) a second proenzyme, or
   (ii) a second activator for the second proenzyme, as the coupled ligand instead of the fully active enzyme;
   inducing a third-stage catalysis by providing the remaining complementary second proenzyme or second activator so as to afford a catalytic activation of the second proenzyme to a second enzyme when the assayed substance is present;
   inducing a second-stage catalysis when the assayed substance is present by providing a first proenzyme capable of being catalytically activated to a first enzyme by the second enzyme;
   inducing a first-stage catalysis when the assayed substance is present by providing a substrate responsive to the first enzyme; and
   measuring the change in said substrate when the assayed substance is present;
   wherein each proenzyme is selected from one of the group consisting of inactive or less active forms of enzymes which are transferases or hydrolases, or active forms of any enzymes encapsulated in liposomes, whereby the sensitivity of the assay is geometrically increased by the multiplication of the third-stage turnover rate, the second-stage turnover rate, and the first-stage turnover rate.

2. The improvement of claim 1 wherein the coupled ligand is the second activator for the second proenzyme.

3. The improvement of claim 1 wherein a four-stage cascade assay is performed by additionally:
using either one of the complement pair of
(i) a third proenzyme, or
(ii) a third activator for the third proenzyme, as the coupled ligand instead of the fully active enzyme,
inducing a fourth-stage catalysis by providing the remaining complementary third enzyme or third activator so as to afford a catalytic activation of the third proenzyme to a third enzyme when the assayed substance is present; and
inducing the third-stage catalysis by providing a second proenzyme capable of being catalytically activated to the second enzyme by the third enzyme; whereby the sensitivity of the assay is geometrically increased by the multiplication of the fourth-stage turnover rate, the third-stage turnover rate, the second-stage turnover rate, and the first-stage turnover rate.

4. The improvement of claim 3 wherein the coupled ligand is the third activator for the third proenzyme.

5. The improvement of claim 1 or 3 wherein the hydrolases are peptide hydrolases and the enzyme encapsulated in a liposome is an oxidoreductase.

6. The improvement of claim 5 wherein the peptide hydrolases are serine proteases or carboxyl proteases.

7. The assay of claim 1 wherein:
the second proenzyme is pepsinogen A, B, or C;
the second activator is carbonic anhydrase or a substance which acidifies the assay;
the second enzyme is pepsin A, B, or C which acts as the first activator;
the first proenzyme is chymotrypsinogen A, B, or C;
the first enzyme is chymotrypsin A, B, or C; and
the substrate is an aminoacyl ester or an aminoacyl amide, or is N-tosyl-L-leucine chlormethyl ketone if the first enzyme is chymotrypsin C, or any of these substrates with a marking label.

8. The assay of claim 7 wherein the aminoacyl ester or aminoacyl amide substrate is:
N-acetyl-L-tryptoplasmin amide; N-benzyloxy carboxyl-L-tyrosine-p-nitrophenyl ester; 7-glutaryl-phenylalanineamido-4-methylcoumarin; or any of these substrates with a marking label.

9. The assay of claim 1 wherein:
the second proenzyme is trypsinogen;
the second activator is enterokinase, trypsinogen kinase, or peptidase A;
the second enzyme is trypsin which acts as the first activator;
the first proenzyme is chymotrypsinogen A, B, or C;
the first enzyme is chymotrypsin A, B, or C; and
the subtrate is an aminoacyl ester or an aminoacyl amide, or is N-tosyl-L-leucine chlormethyl ketone if the first enzyme is chymotrypsin C, or any of these substrates with a marking label.

10. The assay of claim 9 wherein the aminoacyl ester or aminoacyl amide substrate is:
N-acetyl-L-tryptoplasmin amide; N-benzyloxy carboxyl-L-tyrosine-p-nitrophenyl ester; 7-glutaryl-phenylalanineamido-4-methyleoumarin; or any of these substrates with a marking label.

11. The assay of claim 1 wherein:
the second proenzyme is plasminogen;
the second activator is streptokinase, urokinase, staphylokinase, cytofibrokinase, or plasmakinase;
the second enzyme is plasmin which acts as the first activator;
the substrate is fibrinogen with or without a marking label;
the cleaved substrate product is fibrin with or without a marking label; and
the amount of fibrin is measured without the use of a further substrate.

12. The assay of claim 1 wherein:
the second proenzyme is prothrombin;
the second activator is thrombokinase or prothrombin-activating proteinase;
the second enzyme is thrombin which acts as the first activator;
the substrate is fibrinogen with or without a marking label;
the cleaved substrate product is fibrin with or without a marking label; and
the amount of the fibrin is measured without the use of a further substrate.

13. The assay of claim 1 wherein:
the second proenzyme is prokallikrein;
the second activator is Factor XIIa;
the second enzyme is kallikrein which acts as the first activator;
the first proenzyme is kininogen with or without a marking label;
the first enzyme is kinin with or without a marking label; and
the amount of kinin is measured without the use of a substrate.

14. The assay of claim 1 wherein:
the second proenzyme is inactive phosphorylase kinase;
the second activator is protein kinase;
the second enzyme is activated phosphorylase kinase which acts as the first activator;
the first proenzyme is phosphorylase b;
the first enzyme is phosphorylase a; and
the substrate is glycogen with or without a marking label.

15. The assay of claim 1 wherein:
the second proenzyme is inactive angiotensinogen;
the second activator is renin;
the second enzyme is partially active angiotensin I which acts as the first proenzyme;
the first activator is dipeptidyl carboxypeptidase;
the first enzyme is fully activated angiotensin II; and
the substrate is kaolin with or without a marking label.

16. A cascade amplification enzyme immunoassay kit for performing the improved assay of claim 1 consisting essentially of:
(a) an immuno-reactive substance which will react with an assayed substance when said substance is present, said immuno-reactive substance having a coupled ligand which is either one of the complement pair of (1) a second proenzyme capable of activation to a second enzyme, or (2) a second activator for the second proenzyme;
(b) the uncoupled remaining member of the complement pair;

(c) an uncoupled first proenzyme capable of being catalytically activated to a first enzyme by the second enzyme; and
(d) a substrate capable of being catalytically acted upon by the first enzyme; each reagent being present in an amount sufficient to perform at least one assay, so that if the assayed substance is present the immuno-reactive substance with the coupled ligand will bind to it and also be present, the second proenzyme will become catalytically activated to a second enzyme, the second enzyme will catalytically activate the first proenzyme to a first enzyme, and the first enzyme will catalytically act upon the substrate, thereby effecting a three-fold cascade.

17. The improved kit of claim 16 wherein the coupled ligand is the second activator.

* * * * *